United States Patent
Barra et al.

(10) Patent No.: US 6,221,063 B1
(45) Date of Patent: Apr. 24, 2001

(54) METHOD OF ADMINISTERING CARDIOPLEGIA SOLUTION

(75) Inventors: Jean-Aubert Barra, Brest Cedex (FR); William Morris Booth, Paw Paw, MI (US); Carolyn Rose Bocheff, Belmont, MI (US); Donald R. Sandmore, Newaygo, MI (US); Frederick A. Shorey, East Grand Rapids, MI (US); Ernest J. Rodriguez, Rockford, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/313,149

(22) Filed: May 17, 1999

Related U.S. Application Data (62) Division of application No. 08/780,631, filed on Jan. 8, 1997.

(51) Int. Cl.[7] ............................................. A61M 31/00
(52) U.S. Cl. ................................................................ 604/506
(58) Field of Search ............................. 604/96.01, 264, 604/200, 500, 506–509; 606/191, 192, 194, 195, 196

(56) References Cited

U.S. PATENT DOCUMENTS

| | | |
|---|---|---|
| 4,019,515 | 4/1977 | Kornblum et al. . |
| 4,057,065 | 11/1977 | Thow . |
| 4,180,076 | 12/1979 | Betancourt . |
| 4,573,966 | 3/1986 | Weikl et al. . |
| 4,624,657 | 11/1986 | Gould et al. . |
| 4,642,092 | 2/1987 | Moss . |
| 4,648,384 | 3/1987 | Schmukler . |
| 4,689,041 | 8/1987 | Corday et al. . |
| 4,714,460 | 12/1987 | Calderon . |
| 4,796,626 | 1/1989 | DeVries . |
| 4,832,028 | 5/1989 | Patel . |
| 4,867,742 | 9/1989 | Calderon . |
| 5,021,045 | 6/1991 | Buckberg et al. . |
| 5,024,668 | 6/1991 | Peters et al. . |
| 5,033,998 | 7/1991 | Corday et al. . |
| 5,042,976 | 8/1991 | Ishitsu et al. . |
| 5,071,405 | 12/1991 | Piontek et al. . |
| 5,078,681 | 1/1992 | Kawashima . |

(List continued on next page.)

FOREIGN PATENT DOCUMENTS

| | | |
|---|---|---|
| 318 918 | 6/1989 | (EP) . |
| 2 006 624 | 5/1979 | (GB) . |

OTHER PUBLICATIONS

Gumersindo Blanco, MD, Alberto Adam, MD, and Agustin Fernandez, BS, A Direct Experimental Approach to the Aortic Valve, pp. 171–177, Journal of Thoracic Surgery, Aug. 1956.

(List continued on next page.)

Primary Examiner—Sharon Kennedy
Assistant Examiner—Ann Y. Lam
(74) Attorney, Agent, or Firm—Foley & Lardner (57) ABSTRACT

An improved balloon catheter has a catheter body with an expandable member, such as a balloon, mounted to the exterior surface thereof. Preferably, means for preventing sticking of the expandable balloon to the exterior surface of the catheter body are provided. In one aspect, the catheter has an expandable member, preferably a balloon, positioned substantially equidistant from the proximal and distal ends of the catheter body. The retention catheter is positioned externally of the heart and partially surrounds the heart so that the balloon is positioned immediately adjacent the coronary sinus and when inflated, the balloon bears against the coronary sinus and at least one of the inferior vena cava and diaphragm thereby preventing inadvertent movement or removal of the RCSP catheter from the coronary sinus.

13 Claims, 7 Drawing Sheets

U.S. PATENT DOCUMENTS

| | | |
|---|---|---|
| 5,197,952 | 3/1993 | Marcadis et al. . |
| 5,250,025 | 10/1993 | Sosnowski et al. . |
| 5,308,319 | 5/1994 | Ide et al. . |
| 5,385,548 | 1/1995 | Williams et al. . |
| 5,395,330 | 3/1995 | Marcadis et al. . |
| 5,478,309 | 12/1995 | Sweezer et al. . |
| 5,505,698 | 4/1996 | Booth et al. . |
| 5,509,897 | 4/1996 | Twardowski et al. . |
| 5,536,251 | 7/1996 | Evard et al. . |
| 5,849,005 * | 12/1998 | Garrison et al. ............... 606/1 |
| 6,033,379 * | 3/2000 | Barra et al. ................ 604/96 |

OTHER PUBLICATIONS

Vincent L. Gott, MD et al., Retrograde Perfusion of the Coronary Sinus . . . , Surgery, Gynecology & Obstetrics, Mar. 1957, pp. 319–329.

Philippe Menasché , MD et al., Retrograde Coronary Sinus Perfusion: A Safe Alternative for Ensuring Cardioplegic Delivery . . . , Annals of Thoractic Surgery, pp. 647–658 (1982).

Philippé Menasche and Armand H. Piwnica, Retrograde Coronary Sinus Perfusion, Robert's Textbook Myocardial Protection in Cardiac Surgery, Chapter 15, pp. 251–262 (1987).

A.J. Roberts, An Overview of Myocardial Protection in Open–Heart Surgery, The Coronary Sinus, pp. 247–258 (1984).

C. Walton Lillehei, MD, FCCP et al., The Direct Vision Correction . . . , Diseases of the Chest, vol. 30, No. 2, pp. 123–131 (1956).

PCT Form/ISA/220, International Search Report for Application, PCT/US97/24090; Sep. 7, 1998.

* cited by examiner

METHOD OF ADMINISTERING CARDIOPLEGIA SOLUTION

This application is a divisional of U.S. Application No. 08/780,631, filed on Jan. 8, 1997.

BACKGROUND OF THE INVENTION

1. Field of the Invention

This invention relates to an improved balloon catheter and, more specifically, to a catheter incorporating means adapted to prevent the sticking of the expandable member or balloon to the catheter. In another aspect, the invention relates to a catheter for use in coronary bypass surgery positioned externally of the heart and adapted to assist in the retention of a retrograde cardioplegia solution perfusion ("RCSP") catheter in the coronary sinus.

2. Description of the Related Art

Catheters having an expandable member provided thereon have a wide variety of applications in numerous, different, medical procedures. One known structure for such a catheter comprises an expandable member or balloon provided on the outside surface thereof wherein the balloon is expandable between a retracted state and an expanded state. In the retracted state, the balloon can be a "tight-fitting" balloon which is inflated through the application of a pressurized fluid to the interior of the balloon. One problem inherent with such tight-fitting balloons is the uneven inflation of the balloon upon the application of a pressurized fluid to the balloon interior. In drastic cases, portions of the balloon remain tacked to the exterior surface of the catheter body when the balloon is in the fully-inflated position. This can result in the balloon, in the expanded shape, assuming an undesirable, unpredictable configuration. In addition, tacking of the balloon can result in excessive elongation of portions of the balloon body.

As noted above, balloon catheters have a wide variety of applications, only one of which is used during coronary bypass surgical procedures. Perfusion of a heart during coronary bypass surgery with cardioplegia solution can be performed retrograde, antigrade, or a combination of retro and antigrade. During the retrograde provision process a catheter is first typically inserted into the right atrium through an appropriate incision and then inserted through the ostia into the coronary sinus. Next, an expandable member, such as a balloon which is provided on the catheter, is inflated inside the coronary sinus to occlude this vessel. Cardioplegia solution is forced through the catheter into the coronary sinus to perfuse the heart tissue. Examples of known retrograde catheters are seen in U.S. Pat. No. 5,395,330 issued Mar. 7, 1995 to Marcadis et al. and U.S. Pat. No. 5,505,698 issued Apr. 9, 1996 to Booth et al.

One problem with the known RCSP process is possible movement or dislodging of the RCSP catheter from the coronary sinus as a result of the fluid pressure generated inside the coronary sinus. Excessive movement of the inflated RCSP catheter could result in leaking of cardioplegia solution from the coronary sinus back into the right atrium.

Another problem experienced by some patients during the retrograde perfusion process is insufficient perfusion of the heart tissue as a result of leaking of solution from the middle cardiac vein and the small cardiac vein back into the right atrium. When perfusion solution is allowed to drain from the veins back into the right atrium, the cardioplegia solution being perfused through the tissue will seek the path of least resistance and drain into these veins rather than completely perfusing the heart tissue.

SUMMARY OF THE INVENTION

The improved balloon catheter and method for using the same overcomes the problems of the prior art by providing means for preventing the inadvertent sticking or tacking of the inflatable member to the exterior surface of the catheter as the inflatable member is expanded. The catheter and method for using the same also overcomes the problems of the prior art by providing means for effectively sealing the middle and small cardiac veins during the retrograde perfusion process and also providing means for retaining the RCSP catheter within the coronary sinus during the perfusion process.

In a first aspect, the invention comprises a catheter having an inflatable member, preferably a balloon, mounted to the exterior surface of the catheter. The balloon is adapted for expansion or inflation between an inflated state and a retracted state. Means are provided between at least a portion of the interior surface of the balloon and the exterior surface of the catheter to prevent inadvertent sticking of the balloon body to the catheter as the balloon is inflated. The means for preventing the sticking include injecting a liquid lubricant between the balloon and the catheter body, positioning a spring between the balloon and catheter body, and positioning a fluid-permeable sleeve between the balloon and catheter body. Alternatively, the balloon can be stretched or elongated prior to adhering the balloon to the exterior surface of the catheter. Still another means for preventing sticking of the balloon to the catheter would be roughening the contact surfaces of one of the balloon and catheter body to thereby reduce the effective surface area of contact between these two elements. The roughening can be performed by chemical, mechanical, or electrical processes. The catheter incorporating means to prevent sticking of the balloon to the catheter body can be used in any application in which an expandable member such as a balloon is mounted to the exterior surface of the catheter body and in which it is desirable to prevent sticking of the balloon body to the catheter body during the inflation of the balloon. The preferred application of the invention is for use in a coronary surgical application.

In another aspect, the invention comprises a catheter which is ideally suited for use during the retrograde administration of cardioplegia solution. The catheter preferably comprises a catheter body and an inflatable member such as a balloon mounted to the exterior of the catheter body. The balloon is spaced from the proximal and distal ends of the catheter body a sufficient distance so that the balloon can be positioned immediately adjacent to and intermediate the inferior vena cava and the coronary sinus ostia during the retrograde administration of cardioplegia solution while the proximal and distal ends of the catheter body are positioned above the heart.

In the preferred embodiment, a stopcock is mounted to the proximal end of the catheter body, and a guide wire is selectively received in both the stopcock and the catheter body to provide support and rigidity for proper positioning of the catheter.

In still another aspect, the invention comprises a method for the retrograde administration of cardioplegia solution to the heart through the coronary sinus. A cardioplegia catheter is inserted into the coronary sinus through the coronary sinus ostia. A restriction catheter having a balloon provided thereon is positioned externally of the heart so that the balloon is immediately adjacent to the coronary sinus and at least one of the diaphragm and the inferior vena cava. The restriction catheter balloon is inflated so that the balloon bears against the coronary sinus ostia and one of the diaphragm and inferior vena cava. The inflated balloon restricts the coronary sinus ostia and prevents removal of the cardioplegia catheter during the retrograde administration of cardioplegia solution.

BRIEF DESCRIPTION OF THE DRAWINGS

The invention will now be described with reference to the drawings in which.

DETAILED DESCRIPTION OF THE PREFERRED EMBODIMENTS

Figure 1:
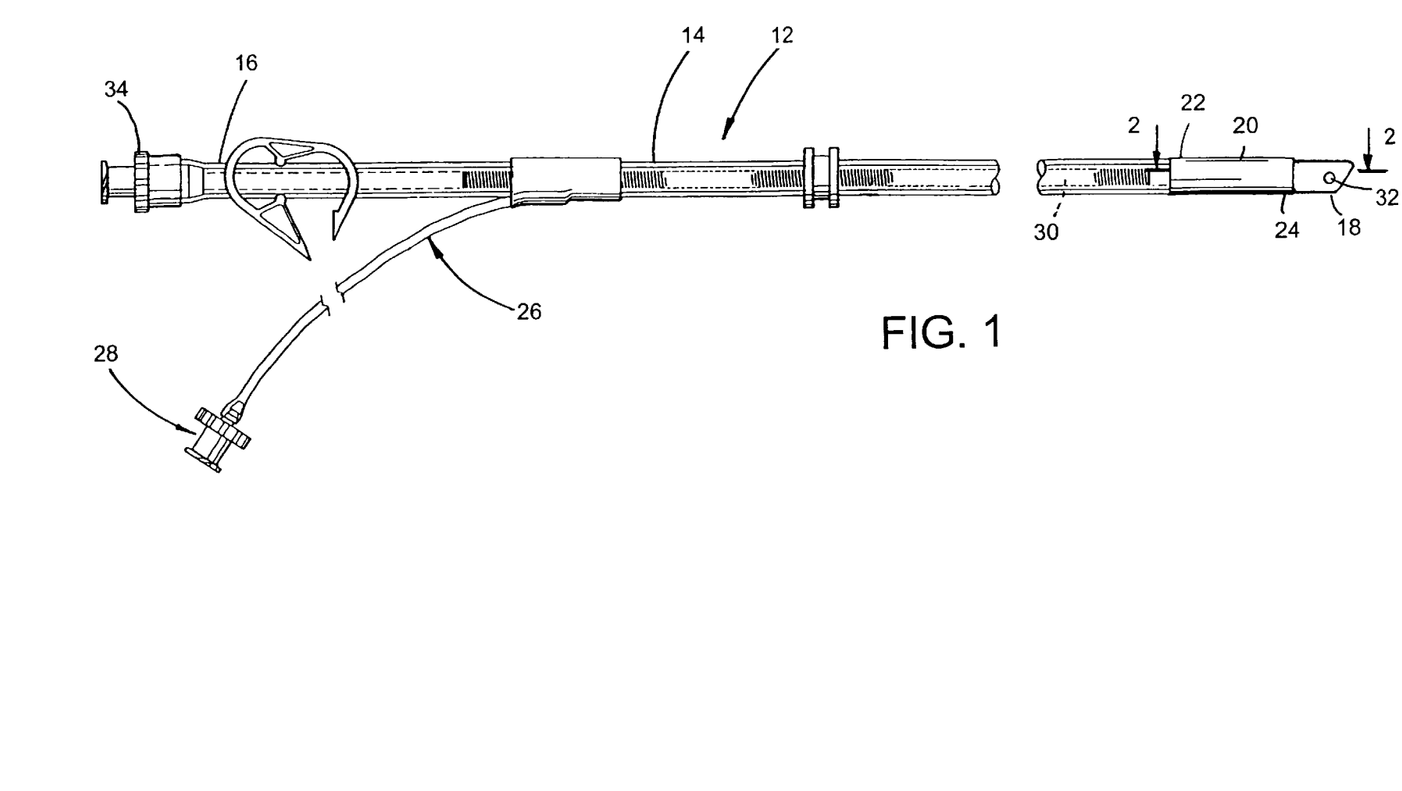
FIG. 1 is a plan view of a first embodiment of the improved balloon catheter according to the invention.
Figure 2:
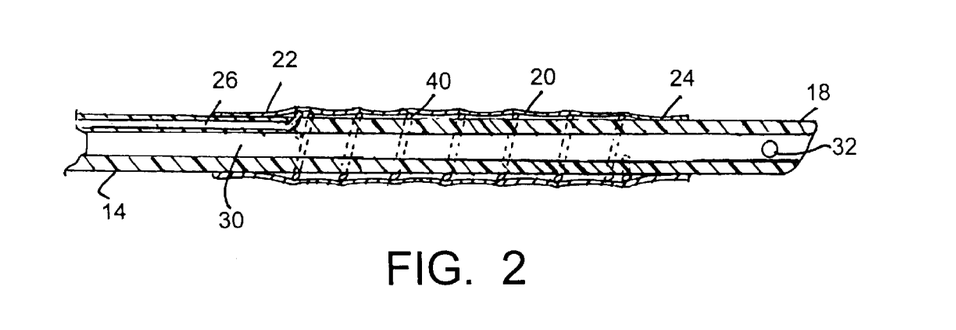
FIG. 2 is a partial, sectional view of the balloon catheter taken along the lines 2—2 of FIG. 1 showing the balloon in the retracted state.
Figure 3:
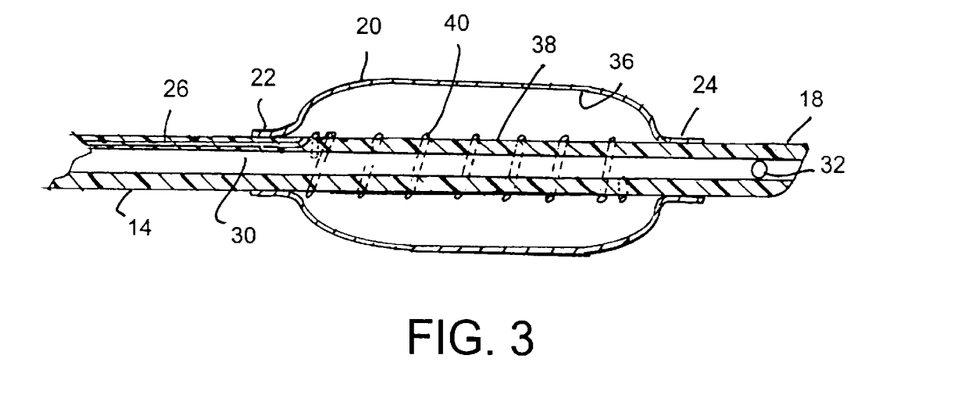
FIG. 3 is a partial, sectional view similar to FIG. 2 showing the balloon in the expanded state.

Referring now to the drawings, and to FIGS. 1–3 in particular, a first embodiment of the catheter 12 according to the invention is shown. In this embodiment, the catheter 12 comprises a catheter body 14 having a proximal end 16, a distal end 18, and an expandable member such as a balloon 20 provided on the exterior surface 38 of the catheter body 14. The proximal 22 and distal ends 24 of the balloon are securely fastened to the exterior surface 38 of the catheter body 14 by suitable means, such as a conventional adhesive. An inflation lumen 26 is provided in the catheter body 14 so that the distal end of the inflation lumen 26 is fluidly connected to the interior of the balloon 20, and the proximal end of the lumen 26 has a conventional luer connector 28 provided thereon to control the fluid flow to the balloon 20. A main lumen 30 extends from the proximal end 16 to the distal end 18 of the catheter body 14. Preferably, multiple fluid apertures 32 are provided adjacent the distal end 18 of the catheter body 14, and a conventional luer connection 34 is provided on the proximal end 16 of the catheter body 14.

The catheter 12 according to the invention is an improvement over the known catheter structures because it includes means to prevent inadvertent sticking or adhesion of the expandable portion of the balloon body 20 to the exterior surface 38 of the catheter body 14. A first embodiment of the means to prevent sticking or adhesion comprises a spring 40 which is positioned on the exterior surface 38 of the catheter body 14 and extends between the proximal 22 and distal ends 24 of the balloon 20. The spring 40 is helically wound around the exterior surface 38 of the catheter body 14 in such a manner to prevent or at least restrict the amount of direct contact between the balloon 20 and the exterior surface 38 of the catheter body 14, intermediate the proximal and distal ends 22, 24 of the balloon 20. The spring is positioned so that it permits the free flow of the inflation fluid through the inflation lumen to the hollow interior of the balloon 20.

In the preferred embodiment of the catheter 12, the catheter body 14 and balloon 20 are both formed from similar, silicon materials. Unfortunately, the use of two, similar, silicon materials can result in the inadvertent sticking of the interior surface of the balloon 20 to the exterior surface of the catheter body 14 as the balloon 20 is inflated. The spring 40 according to the invention overcomes these problems by preventing or restricting contact between the interior surface of the expandable portion of the balloon and the exterior surface of the catheter body 14.

Figure 4:
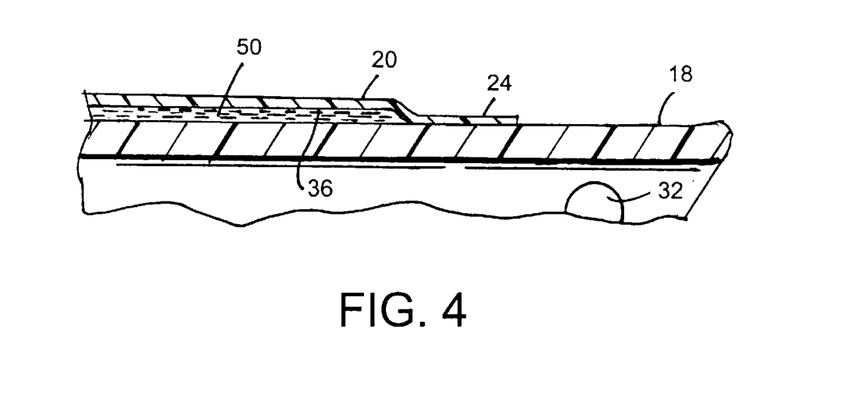
FIG. 4 is a sectional view similar to FIG. 2 showing a second embodiment of the non-sticking catheter according to the invention.

FIG. 4 shows a second embodiment of the means for preventing inadvertent sticking of the balloon 20 to the catheter body 14. In this embodiment, a compatible liquid lubricant 50 is injected into the space between the interior surface 36 of the balloon 20 and the exterior surface 38 of the catheter body 14. The lubricant prevents inadvertent sticking or contact between the balloon 20 and catheter body 14. Preferably, the lubricant 50 is selected from materials which will achieve the desired benefit of preventing sticking without having an adverse impact on the materials selected for the balloon 20 and catheter body 14. Examples of suitable liquid lubricants include glycerin and hydrogel coatings such as polyvinylpyrrolidone, silicone oil, and polydimethyl siloxane.

Figure 5:
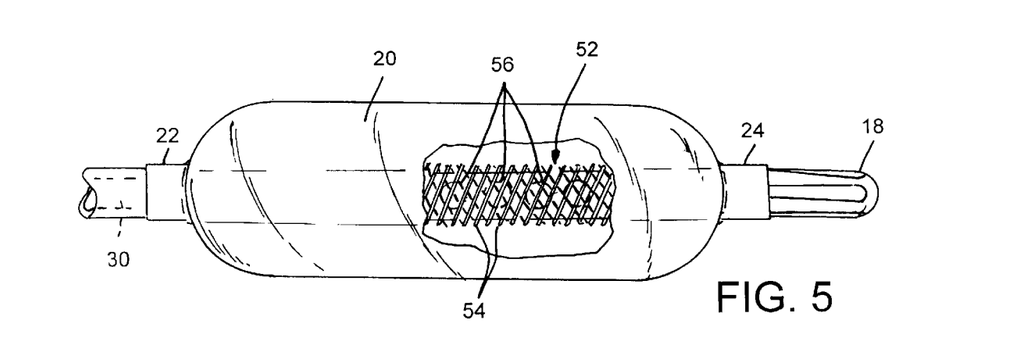
FIG. 5 is a partial, sectional view of the catheter according to the invention showing the balloon in a partially-inflated state with a portion of the balloon broken away to expose a third embodiment of the non-sticking means.

The inflatable balloons shown in FIGS. 1–4 are manually inflated, whereas the balloons which will be shown in FIGS. 5–8 are auto-inflate balloons. The auto-inflate balloon depicted in FIG. 5 shows a third embodiment of the non-sticking means according to the invention. In this embodiment, a mesh sleeve 52 is provided intermediate the interior surface 36 of the balloon 20 and the exterior surface 38 of the catheter body. The sleeve has a plurality of filaments 54 interwoven to restrict or prevent contact between the interior surface 36 of the balloon 20 and the exterior surface 38 of the catheter body 14 without restricting fluid flow from the main lumen 30 through the inflation apertures 56 into the balloon 20. Preferably, the sleeve 52 extends between the proximal and distal ends 22, 24 of the balloon 20, and the sleeve 52 is securely adhered to the exterior surface 38 of the catheter body 14 by conventional adhesives. Multiple inflation apertures 56 are provided in the catheter body 14 and fluidly connect the main lumen 30 to the hollow interior of the balloon 20.

Figure 6:
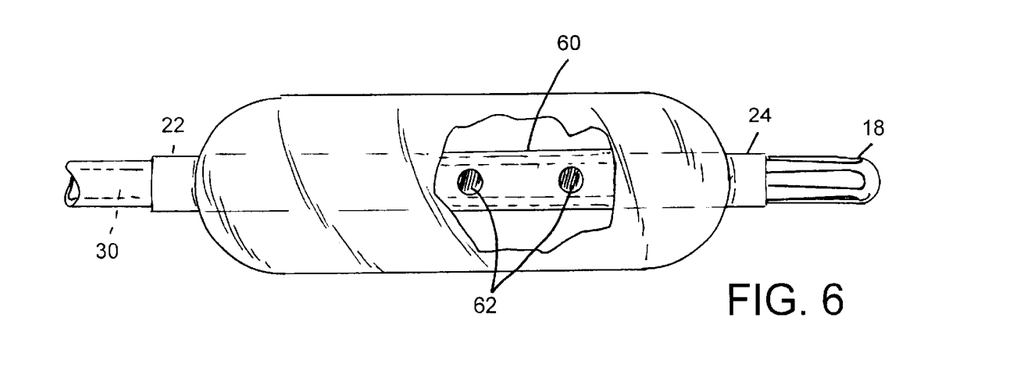
FIG. 6 is a partial, sectional view similar to FIG. 5 showing a fourth embodiment of the non-sticking means.

FIG. 6 shows a fourth embodiment of the non-sticking means according to the invention. In this embodiment, a sleeve 60 having a plurality of fluid apertures 62 formed therein is adhesively mounted to the exterior surface 38 of the catheter body 14 and preferably extends between the proximal and distal ends 22, 24 of the balloon 20. The fluid aperture 62 of the sleeve 60 cooperates with apertures formed in the catheter body 14 to fluidly interconnect the main lumen 30 of the catheter body to the hollow interior of the balloon 20. This embodiment of the non-sticking means is formed by first adhesively mounting a solid sleeve 60 to the exterior surface 38 of the catheter body 14 and then simultaneously forming the fluid aperture 62 in the sleeve 60 and the catheter body 14 by conventional means. Finally, the balloon 20 is mounted to the catheter body 14. With this structure, alignment of the sleeve fluid aperture 62 and apertures in the catheter body is ensured.

Figure 7:
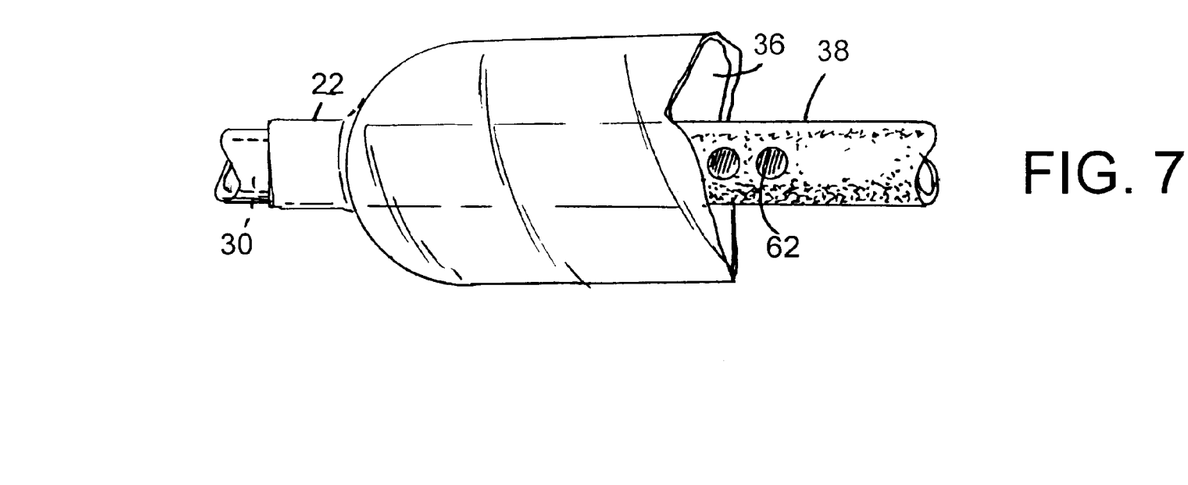
FIG. 7 is a partial, sectional view similar to FIG. 5 showing a fifth embodiment of the non-sticking means.

FIG. 7 shows a fifth embodiment of the non-sticking means according to the invention. In this embodiment, at least one of the exterior surface 38 of the catheter body 14 and the interior surface 36 of the balloon 20 are roughened by conventional means. In FIG. 7, the exterior surface 38 of the catheter body 14 has been roughened to reduce the area of contact between the interior surface 36 of the balloon 20 and the exterior surface 38 of catheter body 14. With this reduced area of contact between the two elements, the likelihood of sticking of the balloon 20 to the catheter body 14 is reduced.

The surfaces of the balloon and catheter body can be roughened by any one of several, conventional methods. For example, the surfaces can be roughened by a chemical process in which the area to be roughened is sprayed, dipped, or wiped with a suitable oxidizing agent which will roughen the surface which is exposed thereto. A plasma oxidizing process is shown in U.S. Pat. No. 5,133,422 which is expressly incorporated herein by reference.

An alternative to the chemical process would be a mechanical roughening of the surface. For example, the surface can be rubbed or scraped with an abrasive material. Alternatively, the surface can be roughened by a conventional, electrical, corona treatment. In this process, the top layer of the surface being treated is ionized through a weak electrical discharge. The ionization of the surface causes release of certain molecules, thereby roughening the surface on a microscopic level.

Figure 8:
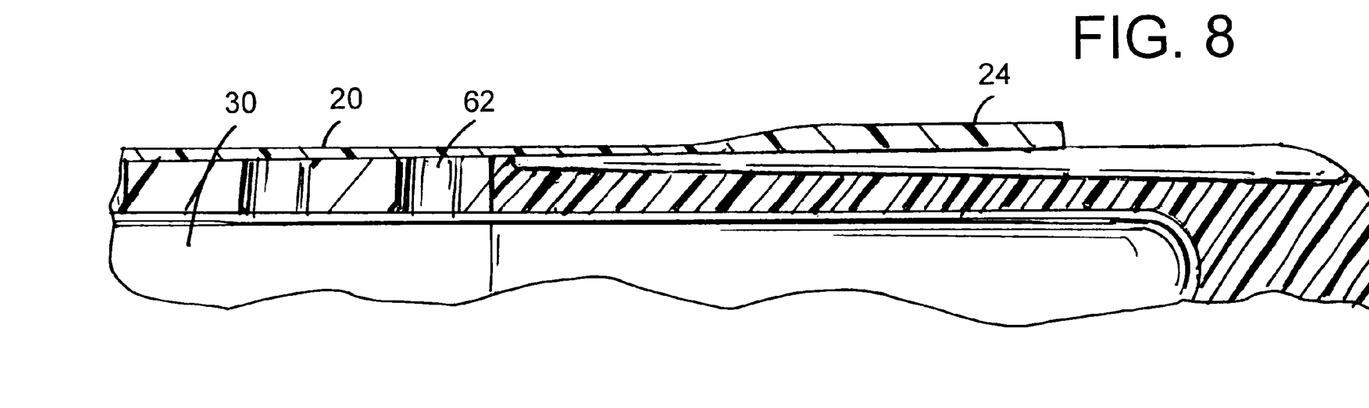
FIG. 8 is a partial, sectional view similar to FIG. 2 showing a sixth embodiment of the non-sticking means according to the invention.

FIG. 8 shows yet another means for avoiding sticking of the balloon 20 to the catheter body 14. In conventional catheter structures, the balloon is mounted to the exterior surface of the catheter body in a substantially relaxed condition. In the embodiment seen in FIG. 8, the balloon 20 is elongated prior to mounting to the exterior surface 38 of the catheter body 14. In this embodiment, the pre-tensioned balloon is less likely to inadvertently stick to the exterior surface of the catheter body because of the stress levels already present in the material. Preferably, the balloon 20 is elongated 50% prior to mounting to the exterior surface 38 of the catheter body 14.

Figure 10:
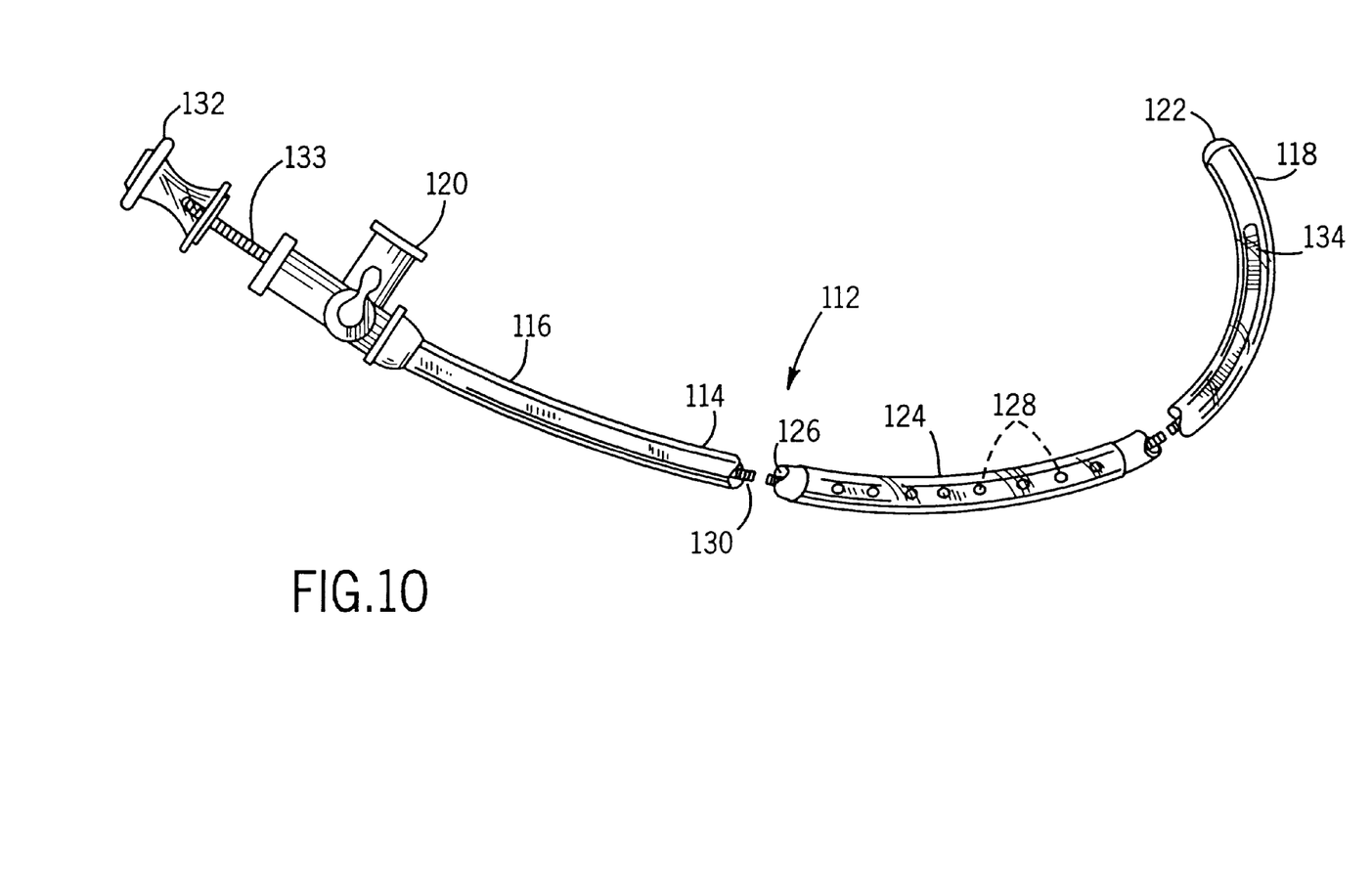
FIG. 10 is a plan view of a preferred embodiment of the retention catheter assembly according to the invention.

Any catheter having an expandable balloon mounted thereto in which the potential exists for the inadvertent sticking or tacking of the balloon to the catheter body can incorporate one or more of the non-sticking means described above. As is apparent to a person skilled in the art, one or more of the nonsticking means can easily be used in a vast number of known catheter structures and applications. The preferred embodiment of the catheter easily adapted to incorporate any one of the non-sticking means is described further below and is particularly suited for use during coronary bypass surgery. In this embodiment, a retention catheter 112 according to the invention comprises a catheter body 114 having a proximal end 116 and a distal end 118. Preferably, a conventional stopcock 120 is provided on the proximal end 116 of the catheter body 114. The distal end 118 preferably comprises a rounded, closed tip 122. An expandable member such as a selectively inflated elastomeric balloon 124 is mounted on the exterior surface of the catheter body 114. A lumen 126 extends through the catheter body 114 from the proximal end 116 to the balloon 124, and the interior of the balloon 124 is fluidly connected to the lumen 126 by a plurality of fluid apertures 128. Preferably, the catheter body is formed from a pliable material such as silicone or polyvinyl chloride, and the balloon 124 is formed from a highly elastic material such as silicone which tightly adheres to the exterior surface of the catheter body 114 in its unexpanded state. Pressurized fluid, supplied from a suitable source, passes through the stopcock 120, lumen 126, and fluid apertures 128 to inflate the balloon 124 to suitable fluid pressures. It is important to note that in the preferred embodiment of the retention catheter, the catheter has only a single lumen and the only outlet of fluid from the lumen 126 is the fluid apertures 128 leading to the closed balloon 124. Therefore, any and all pressurized fluid which is directed into the catheter 112 is directed solely to the inflation or expansion of the balloon 124.

In the preferred embodiment, a guide wire 130 is received inside the catheter lumen 126 for ease of positioning the catheter. However, it is to be understood that the guide wire 130 is not a necessary element of the invention. The guide wire 130 comprises a handle 132 positioned on the proximal end 133 of the guide wire 130. Preferably, the length of the guide wire is dimensioned so that the distal end 134 of the guide wire 130 is immediately adjacent the rounded distal tip 122 of the catheter body 114 when the guide wire 130 is fully received inside the catheter lumen 126. In FIG. 10, the guide wire 130 is shown partially removed from the catheter body 114.

Figure 9:
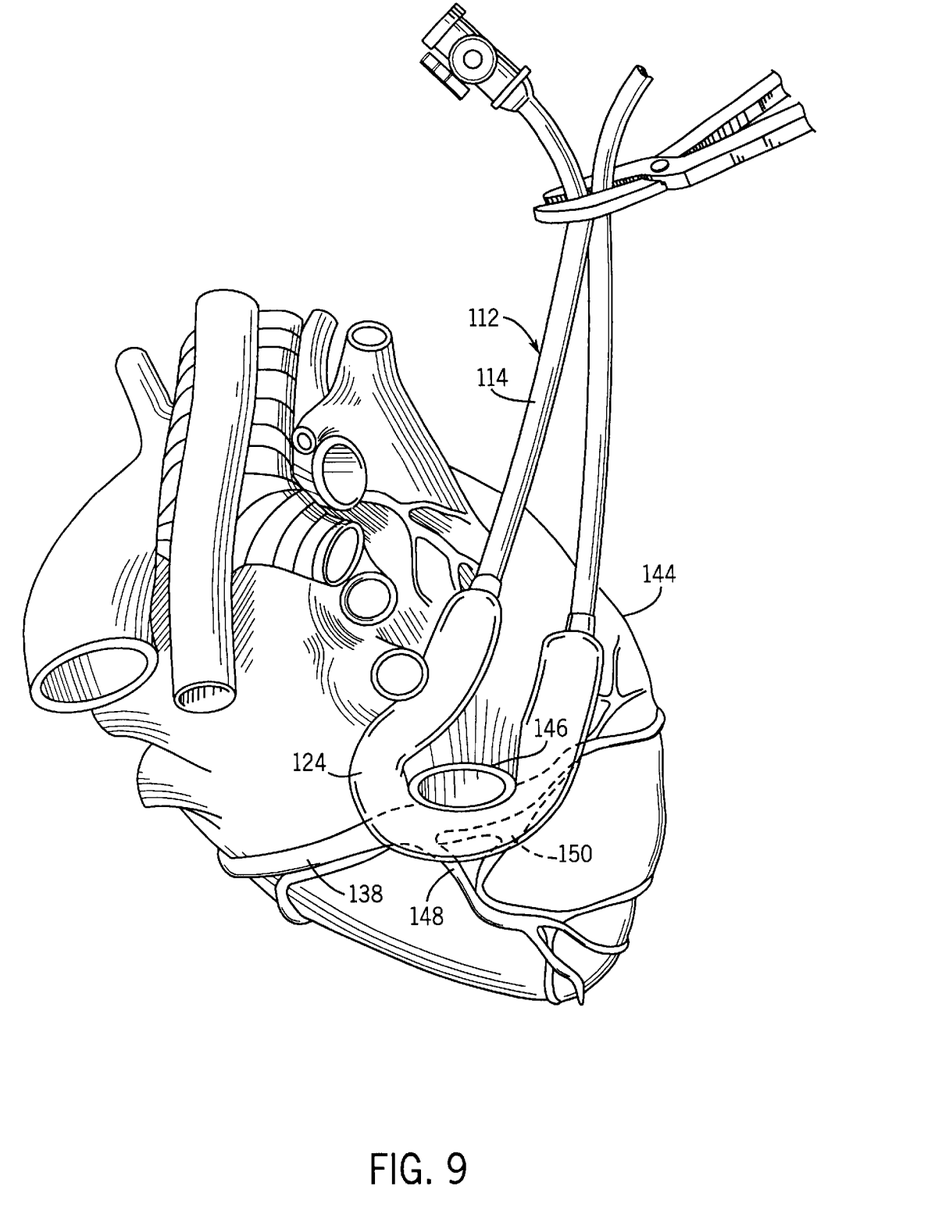
FIG. 9 is a bottom, perspective view of a heart showing a retention catheter according to the invention in position for assisting in the retrograde perfusion process.
Figure 11:
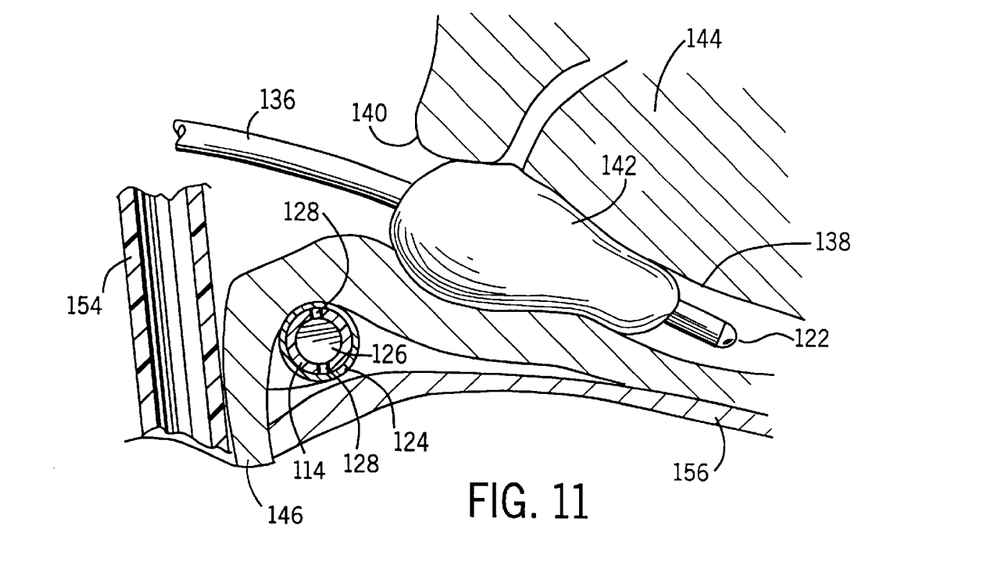
FIG. 11 is a partial, sectional view of a heart showing the retention catheter in position with the expandable member in the deflated state.
Figure 12:
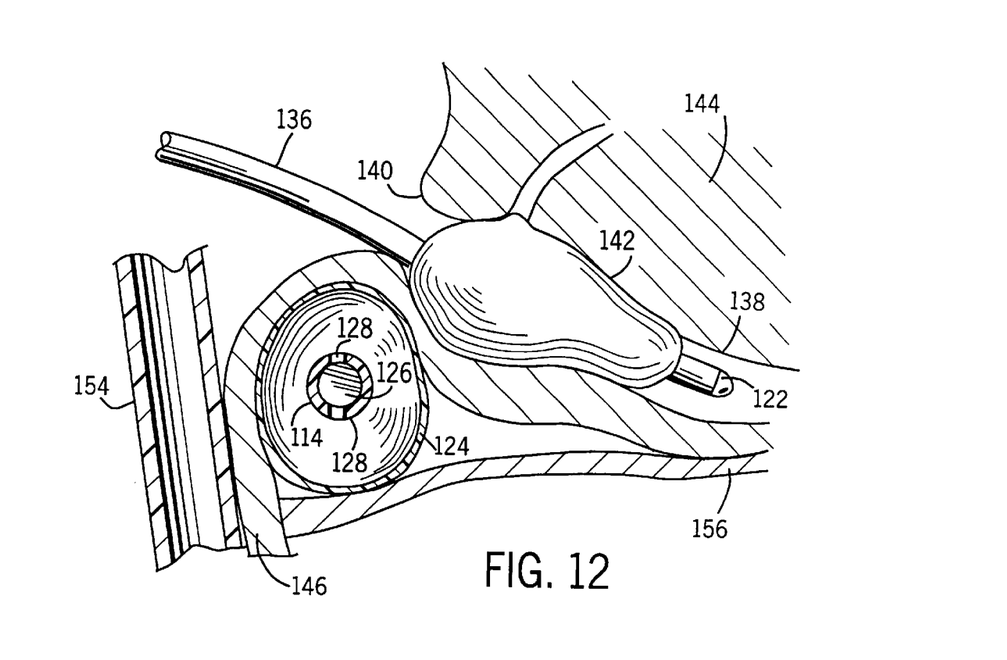
FIG. 12 is a sectional view similar to FIG. 11 showing the retention catheter in position with the expandable member in the inflated state.

The retention catheter 112 is ideally suited for use during the retrograde administration of cardioplegia solution into the coronary sinus. As seen in FIGS. 9, 11, and 12, the process of retrograde administration of cardioplegia solution begins with the step of introducing the RCSP catheter 136 via the right atrium into the coronary sinus 138 through the coronary sinus ostia 140. Preferably, the RCSP catheter 136 is inserted with the balloon 142 in the unexpanded state (not shown). Eventually, the RCSP catheter balloon 142 is inflated, and pressurized cardioplegia solution passes through the catheter 136 into the coronary sinus 138. A preferred embodiment of the RCSP catheter is seen in U.S. Pat. No. 5,505,698 to Booth et al. which is expressly incorporated herein by reference.

Prior to the retrograde administration of cardioplegia solution through the RCSP catheter 136, the retention catheter 112 is positioned externally of the heart 144 for enhancing the retrograde administration of cardioplegia solution. In the preferred method, the distal end 118 of the retention catheter 112 and guide wire 130 assembly is slid underneath the heart 144, preferably inside the percutaneous sack and forced up and around the body of the heart 144 until the balloon 124 of the retention catheter 1 12 is positioned immediately adjacent the inferior vena cava 146, coronary sinus 138, middle cardiac vein 148, and small cardiac vein 150. Preferably, the retention catheter 112 is so positioned with the balloon 124 in the unexpanded state. In this position, the proximal 116 and distal 118 ends of the retention catheter 112 preferably are both positioned above the heart 144 so that the ends can be secured to the surgical drapes or other suitable structure sufficient to hold the catheter 112 in position with respect to the heart 144. Once the catheter is properly positioned, the guide wire 130 is removed therefrom, and then the stopcock 120 is fluidly connected to a suitable source of pressurized fluid for inflation of the balloon.

In most surgical procedures in which the heart is perfused in the retrograde manner, a venous cannula 154 is inserted into the right atrium and the inferior vena cava 146. The cannula 154 is used to draw venous blood from the patient during bypass. FIGS. 11 and 12 depict one example of a venous cannula 154 positioned in the right atrium and inferior vena cava 146. The retention catheter 112 is preferably used simultaneously with a venous cannula 154 positioned in the inferior vena cava 146. However, use of the venous cannula 154 in this process is by no means a necessity.

Once the venous cannula 154 and RCSP catheter 136 are properly in position, the balloon 124 of the retention catheter 112 can be inflated. Pressurized fluid from a suitable source fluidly connected to the proximal end 116 of the catheter body 114 flows through the stopcock 120, the lumen 126, and the fluid apertures 128 resulting in inflation of the balloon 124. As the balloon inflates, it bears against the patient's diaphragm 156, the inferior vena cava 146, and the bottom surface of the heart 144 including the coronary sinus 138, middle cardiac vein 148, and small cardiac vein 150. The diaphragm 156 and inferior vena cava 146 with the cannula 154 received therein are relatively immovable compared to the heart tissue and the several veins. Therefore, as the balloon 124 expands, it compresses the coronary sinus 138 immediately adjacent the sinus ostia 140, the middle cardiac vein 148, and the small cardiac vein 150. With the balloon 124 in the expanded state as seen in FIG. 12, the coronary ostia 140 is pinched partially closed. The partial closure of the ostia prevents the inadvertent removal of the inflated RCSP catheter 136 from the coronary sinus 138. Simultaneous with the pinching of the ostia 140, the middle and small cardiac veins 148, 150 will also be compressed as a result of the expansion of the balloon 124. Preferably, the balloon 124 is inflated a sufficient amount to pinch closed the middle and small cardiac veins 148, 150, thereby preventing cardioplegia solution from passing through either of these veins, back into the right atrium of the heart 144.

In the preferred embodiment, the catheter body 114 is 43 centimeters in total length, and the balloon 124, in the expanded state, is eight centimeters in length. Preferably, the balloon 124 is positioned equidistant along the length of the catheter body 114 so that each end of the balloon 124 is approximately 17.5 centimeters from the corresponding end of the catheter. With this structure, there is sufficient length of the catheter body 114 both proximally and distally from the balloon 124 so that the ends of the catheter body 114 can be easily secured to the surgical drapes and the like for retaining the catheter 112 in position once the balloon 124 has been inflated.

Use of the catheter according to the invention is an improvement over the known balloon catheters because the possibility of the inadvertent sticking of the balloon to the catheter body during inflation is minimized. In addition, use of the retention catheter according to the invention is an improvement over the known methods for the administration of cardioplegia solution in the retrograde manner because inadvertent removal of the RCSP catheter is minimized, and any undesirable draining of cardioplegia solution from the middle and small cardiac veins back into the right atrium is also minimized upon inflation of the properly positioned balloon catheter. These benefits are achieved without any additional incisions or trauma to the heart than that which is already encountered in a standard open heart surgical procedure.

Reasonable variation and modification are possible within the spirit of the foregoing specification and drawings without departing from the scope of the invention.

The embodiments for which an exclusive property or privilege is claimed are defined as follows:

1. A method for the retrograde administration of cardioplegia solution to the heart through the coronary sinus comprising the steps of:
   providing a cardioplegia catheter having a catheter body with a proximal end and a distal end;
   providing a restriction catheter having a catheter body with a proximal end and a distal end, a selectively expandable member provided on an exterior surface of the body, and a lumen adapted to conduct fluid to the expandable member;
   inserting the distal end of the cardioplegia catheter into the coronary sinus through the coronary sinus ostia;
   positioning the expandable member of the restriction catheter externally of the heart, immediately adjacent to the coronary, and intermediate the coronary sinus ostia and a first member;
   dilating the expandable member of the restriction catheter a sufficient amount so that the restriction catheter bears against the first member and the coronary sinus thereby restricting movement of the cardioplegia catheter within the coronary sinus during the retrograde administration of cardioplegia solution through the cardioplegia catheter; and
   providing cardioplegia solution through the cardioplegia catheter.

2. A method for the retrograde administration of cardioplegia solution according to claim 1 and further comprising the steps of:
   providing a selectively expandable member on an exterior surface of the cardioplegia catheter wherein the expandable member is positioned adjacent the distal end, a lumen is provided in the body of the cardioplegia catheter, and a fluid discharge aperture is provided distally of the cardioplegia catheter expandable member and fluidly connected to the lumen; and
   dilating the expandable member of the cardioplegia catheter.

3. A method for the retrograde administration of cardioplegia solution according to claim 2 wherein the cardioplegia catheter expandable member is dilated prior to dilation of the restriction catheter expandable member.

4. A method for the retrograde administration of cardioplegia solution according to claim 2 and further comprising the steps of:
   providing a source of pressurized cardioplegia solution; and
   fluidly connecting both the cardioplegia catheter and the expandable member of the restriction catheter to the source of pressurized cardioplegia solution so that the expandable member of the restriction catheter and the cardioplegia catheter are simultaneously supplied with pressurized cardioplegia solution.

5. A method for the retrograde administration of cardioplegia solution according to claim 1 wherein the first member is selected from the group comprising the diaphragm and the inferior vena cava.

6. A method for the retrograde administration of cardioplegia solution according to claim 5 and further comprising the step of inserting a venous cannula into the inferior vena cava.

7. A method for the retrograde administration of cardioplegia solution according to claim 6 wherein the venous cannula is inserted prior to dilation of the restriction catheter expandable member.

8. A method for the retrograde administration of cardioplegia solution according to claim 6 wherein the venous cannula is inserted prior to positioning of the restriction catheter.

9. A method for the retrograde administration of cardioplegia solution according to claim 6 wherein the venous cannula is inserted subsequent to positioning of the restriction catheter.

10. A method for the retrograde administration of cardioplegia solution according to claim 1 and further comprising the steps of:

provuding a source of pressurized cardioplegia solution; and fluidly connecting both the cardioplegia catheter and the expandable member of the restriction catheter to the source of pressurized cardioplegia solution so that the cardioplegia catheter and the expandable member of the restriction catheter are simultaneously supplied with pressurized cardioplegia solution.

11. A method of restricting movement of a member positioned inside the coronary sinus of a heart comprising the steps of:

providing a restriction catheter having a catheter body with a proximal end, a distal end, a selectively expandable member provided on an exterior surface of the body, and a lumen extending through at least a portion of the catheter body which is adapted to conduct fluid to the expandable member;

positioning the restriction catheter externally of the heart so that the expandable member is immediately adjacent to the coronary sinus ostia and intermediate the coronary sinus ostia and a first member;

dilating the expandable member a sufficient amount so that the expandable member bears against the fixed member and the coronary sinus and at least partially constricts the ostia of the coronary sinus thereby preventing inadvertent extraction of the expandable member from the coronary sinus.

12. A method of restricting movement of a member according to claim 11 wherein the first member comprises the diaphragm.

13. A method of restricting movement of a member according to claim 11 wherein the fixed member comprises the inferior vena cava.

* * * * *